United States Patent
Sundermann et al.

(10) Patent No.: US 7,064,236 B2
(45) Date of Patent: Jun. 20, 2006

(54) SUBSTITUTED 1-ARYL-BUT-3-ENYLAMINE AND 1-ARYL-BUT-2-ENYLAMINE COMPOUNDS

(75) Inventors: Bernd Sundermann, Aachen (DE); Corinna Sundermann, Aachen (DE); Helmut Buschmann, Esplugues de Llobregat (ES); Babette-Yvonne Koegel, Langerwehe-Hamich (DE)

(73) Assignee: Grunenthal GmbH, Aachen (DE)

( * ) Notice: Subject to any disclaimer, the term of this patent is extended or adjusted under 35 U.S.C. 154(b) by 141 days.

(21) Appl. No.: 10/751,585

(22) Filed: Jan. 5, 2004

(65) Prior Publication Data

US 2004/0171615 A1  Sep. 2, 2004

Related U.S. Application Data

(63) Continuation of application No. PCT/EP02/07381, filed on Jul. 3, 2002.

(30) Foreign Application Priority Data

Jul. 5, 2001  (DE) .............................. 101 32 747

(51) Int. Cl.
*C07C 215/42* (2006.01)
*C07C 215/46* (2006.01)
*C07C 215/48* (2006.01)
*C07C 211/01* (2006.01)
*C07C 211/16* (2006.01)

(52) U.S. Cl. .................... 564/355; 564/356; 564/363; 564/366; 514/649; 514/653

(58) Field of Classification Search ................ 564/355
See application file for complete search history.

(56) References Cited

U.S. PATENT DOCUMENTS 3,564,100 A   2/1971  Frankus et al. ............. 424/330
5,811,582 A   9/1998  Buschmann et al. ........ 564/355

FOREIGN PATENT DOCUMENTS

DE        963424       5/1957
DE     19915601 A1    10/2000

OTHER PUBLICATIONS

"Partly Reduced Biphenyls As Central Nervous System Agents. 1.4-Arylcyclohex-3-enylamines", Lednicer et al., Journal of Medicinal Chemistry, vol. 15, No. 12, 1972, pp. 1235–1238.

*Primary Examiner*—Brian Davis
(74) *Attorney, Agent, or Firm*—Perman & Green, LLP.

(57) ABSTRACT

The invention relates to substituted 1-aryl-but-3-enylamine and 1-aryl-but-2-enylamine compounds, to a method for the production thereof, to medicaments containing said compounds and to their use in the production of medicaments.

34 Claims, No Drawings

SUBSTITUTED 1-ARYL-BUT-3-ENYLAMINE AND 1-ARYL-BUT-2-ENYLAMINE COMPOUNDS

This application is a continuation of international application number PCT/EP02/07381 filed Jul. 3, 2002, status pending.

The present invention relates to substituted 1-aryl-but-3-enylamine and 1-aryl-but-2-enylamine compounds, a process for the production thereof, pharmaceutical preparations containing these compounds and the use of these compounds for the production of pharmaceutical preparations.

Pain is one of the basic clinical symptoms. There is a worldwide need for effective pain treatments. The urgency of the requirement for effective therapeutic methods for providing tailored and targeted treatment of chronic and non-chronic pain, this being taken to mean pain treatment which is effective and satisfactory from the patient's standpoint, is evident from the large number of scientific papers relating to applied analgesia and to basic nociception research which have appeared in recent times.

Conventional opioids, such as for example morphine, are effective in the treatment of severe to very severe pain. However, they produce accompanying symptoms which include respiratory depression, vomiting, sedation, constipation and development of tolerance. Research is being carried out worldwide into other pain-relieving agents.

The object of the present invention was accordingly to provide new compounds which are particularly suitable as pharmaceutical active ingredients in pharmaceutical preparations.

These active ingredients are intended in particular to combat pain. Moreover, the active ingredients are also intended to be suitable for the treatment of depression, hypotension, hypertension, senile dementia, Alzheimer's disease, general cognitive dysfunction, tinnitus, hardness of hearing, epilepsy, obesity, cachexia, urinary incontinence or anxiolysis or diuresis.

According to the invention, this object is achieved by the provision of substituted 1-aryl-but-3-enylamine and 1-aryl-but-2-enylamine compounds of formula I below, which exhibit a pronounced analgesic effect and which are also suitable in particular for the treatment of depression, hypotension, hypertension, senile dementia, Alzheimer's disease, general cognitive dysfunction, tinnitus, hardness of hearing, epilepsy, obesity, cachexia, urinary incontinence or anxiolysis or diuresis.

The present invention accordingly provides substituted 1-aryl-but-3-enylamine and 1-aryl-but-2-enylamine compounds of the general formula I,

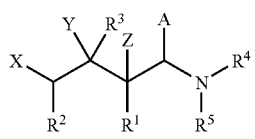

I in which $R^1$ and $R^2$, identical or different, denote a $C_{1-6}$ alkyl residue or together form a $(CH_2)_{2-6}$ ring, which may also be substituted or benzo-fused with at least one optionally at least mono-substituted aryl or heteroaryl residue, preferably together form a $(CH_2)_{2-6}$ ring, which may also be substituted or benzo-fused with at least one optionally at least mono-substituted aryl or heteroaryl residue, particularly preferably together form a cyclohexyl ring, which may also be substituted with an optionally at least mono-substituted phenyl residue, $R^3$ denotes a $C_{3-6}$ alkyl, a $C_{3-7}$ cycloalkyl, an optionally at least mono-substituted aryl or heteroaryl residue or an optionally at least mono-substituted aryl or heteroaryl residue attached via a $C_{1-3}$ alkylene group, preferably an optionally at least mono-substituted aryl residue or an optionally at least mono-substituted aryl residue attached via a $C_{1-3}$ alkylene group, particularly preferably an optionally at least mono-substituted phenyl, benzyl or phenethyl residue, $R^4$ and $R^5$, identical or different, denote a $C_{1-6}$ alkyl, a $C_{3-7}$ cycloalkyl, a phenyl, a benzyl or a phenethyl residue or $R^4$ and $R^5$ together form a $(CH_2)_{3-6}$ or $-CH_2-CH_2-O-CH_2-CH_2-$ ring, preferably, identical or different, denote a $C_{1-6}$ alkyl residue or together form a $-(CH_2)_5-$ or $-CH_2-CH_2-O-CH_2-CH_2-$ ring, particularly preferably, identical or different, denote a $C_{1-2}$ alkyl residue, X and Y or Y and Z together denote a bond, preferably X and Y together denote a bond, A denotes an optionally at least mono-substituted aryl or heteroaryl residue, preferably an optionally at least mono-substituted aryl residue, particularly preferably an optionally at least mono-substituted phenyl residue, in the form of the racemates, diastereomers or enantiomers thereof as a free base or a corresponding physiologically acceptable salt.

The term "alkyl residue" includes for the purposes of the present invention linear or branched hydrocarbon residues. The alkyl residues are preferably selected from the group consisting of methyl, ethyl, propyl, isopropyl, n-butyl, sec.-butyl, tert.-butyl, n-pentyl, neopentyl and n-hexyl.

The term "aryl residue" includes for the purposes of the present invention aromatic hydrocarbons. If the aryl residue comprises more than one substituent, these may be identical or different. The aryl residue is preferably a phenyl residue optionally at least mono-substituted with F, Cl, Br, $CHF_2$, $CF_3$, OH, $OCF_3$, $OR^6$, $NR^7R^8$, $SR^6$, phenyl, $SO_2-CH_3$, $SO_2-CF_3$, $C_{1-6}$ alkyl, CN, $COOR^6$, $CONR^7R^8$, in which $R^6$ denotes a $C_{1-6}$ alkyl, a phenyl, a benzyl or a phenethyl residue, $R^7$ and $R^8$, identical or different, denote H, a $C_{1-6}$ alkyl, a phenyl, a benzyl or a phenethyl residue.

Two substituents of the aryl residue may also form a saturated or unsaturated hydrocarbon ring optionally comprising heteroatoms on the aryl residue, preferably an $-OCH_2O-$, $-OCH_2CH_2O-$, $-CH=CHO-$, $-CH=C(CH_3)O-$ or $-(CH_2)_4-$ ring. Likewise preferred is a substituted phenyl residue, whose two substituents form an $-OCH_2O-$, $-OCH_2CH_2O-$, $-CH=CHO-$, $-CH=C(CH_3)O-$ or $-(CH_2)_4-$ ring.

The term "cycloalkyl residue" includes for the purposes of the present invention saturated cyclic hydrocarbon residues or alkyl residues, which comprise such a sub-structure. Preferably the cycloalkyl residues are selected from the group consisting of cyclopropyl, cyclopropylmethyl, methylcyclopropyl, cyclobutyl, 1-cyclopropylethyl, 2-cyclopropylethyl, cyclopentyl, cyclopentylmethyl, cyclohexyl and cycloheptyl.

The term "heteroaryl residue" denotes for the purposes of the present invention a preferably 5- or 6-membered cyclic aromatic residue, which comprises one or more heteroatoms if the heteroaryl residue comprises more than one heteroatom, these may be identical or different. The heteroatoms selected from the group consisting of nitrogen, oxygen and sulfur are preferred.

If the heteroaryl residue comprises more than one substituent, these may be identical or different.

The heteroaryl residue is preferably an optionally at least mono-substituted furanyl, thiophenyl, pyrrolyl, pyridine, pyrimidinyl, quinolinyl, isoquinolinyl, phthalazinyl or quinazolinyl residue.

The heteroaryl residue may preferably be mono- or polysubstituted with a substituent selected from the group consisting of F, Cl, Br, $CHF_2$, $CF_3$, OH, $OCF_3$, $OR^6$, $NR^7R^8$, $SR^6$, phenyl, $SO_2$—$CH_3$, $SO_2$—$CF_3$, $C_{1-6}$ alkyl, CN, $COOR^6$ and $CONR^7R^8$, in which the residues $R^6$, $R^7$ and $R^8$ have the above-stated meaning.

Two substituents of the heteroaryl residue may also form a saturated or unsaturated hydrocarbon ring optionally comprising heteroatoms on the heteroaryl residue, preferably an —$OCH_2O$—, —$OCH_2CH_2O$—, —CH=CHO—, —CH=C($CH_3$)O— or —$(CH_2)_4$ring.

The following substituted 1-aryl-but-3-enylamine and 1-aryl-but-2-enylamine compounds and the corresponding physiologically acceptable salts thereof, preferably the hydrochlorides thereof, are very particularly preferred:

Dimethyl-[phenyl-(2-phenyl-cyclohex-1-enyl)-methyl]-amine,
{[2-(4-Chloro-phenyl)-cyclohex-1-enyl]-phenyl-methyl}-dimethyl-amine,
[(2-Benzyl-cyclohex-1-enyl)-phenyl-methyl]-dimethyl-amine,
{[2-(4-Fluoro-3-methyl-phenyl)-cyclohex-1-enyl]-phenyl-methyl}-dimethyl-amine,
Dimethyl-[phenyl-(2-o-tolyl-cyclohex-1-enyl)-methyl]-amine,
[(2-Cyclopentyl-cyclohex-1-enyl)-phenyl-methyl]-dimethyl-amine,
Dimethyl-[phenyl-(2-m-tolyl-cyclohex-1-enyl)-methyl]-amine,
(Bicyclohexyl-1-en-2-yl-phenyl-methyl)-dimethyl-amine,
{[2-(4-Fluoro-phenyl)-cyclohex-1-enyl]-phenyl-methyl}-dimethyl-amine,
Dimethyl-[(2-phenethyl-cyclohex-1-enyl)-phenyl-methyl]-amine,
{[2-(3-Methoxy-phenyl)-cyclohex-1-enyl]-phenyl-methyl}-dimethyl-amine,
Dimethyl-{phenyl-[2-(3-phenyl-propyl)-cyclohex-1-enyl]-methyl}-amine,
{[2-(2-Chloro-benzyl)-cyclohex-1-enyl]-phenyl-methyl}-dimethyl-amine,
{[2-(4-Fluoro-benzyl)-cyclohex-1-enyl]-phenyl-methyl}-dimethyl-amine,
{[2-(3-Methoxy-benzyl)-cyclohex-1-enyl]-phenyl-methyl}-dimethyl-amine,
{[2-(3-Fluoro-benzyl)-cyclohex-1-enyl]-phenyl-methyl}-dimethyl-amine,
{[2-(2-Methoxy-benzyl)-cyclohex-1-enyl]-phenyl-methyl}-dimethyl-amine,
{[2-(3,5-Difluoro-cyclohex-1-enyl]-phenyl-methyl}-dimethyl-amine,
{[2-(2-Fluoro-benzyl)-cyclohex-1-enyl]-phenyl-methyl}-dimethyl-amine,
{[2-(2-Chloro-benzyl)-cyclohex-1-enyl]-phenyl-methyl}-dimethyl-amine,
{[2-(3-Fluoro-benzyl)-cyclohex-1-enyl]-phenyl-methyl}-dimethyl-amine,
Dimethyl-{phenyl-[2-(3-trifluoromethyl-benzyl)-cyclohex-1-enyl]-methyl}-amine,
Dimethyl-[(2-phenethyl-cyclohex-1-enyl)-phenyl-methyl]-amine,
3-[6-(Dimethylamino-phenyl-methyl)-cyclohex-1-enyl]-phenol,
Dimethyl-{phenyl-(2-(4-trifluoromethylphenyl)-cyclohex-1-enyl]-methyl}-amine,
2-Chloro-5-[6-(dimethylamino-phenyl-methyl)-cyclohex-1-enyl]-phenol,
{[2-(4-Methoxy-phenyl)-cyclohex-2-enyl]-phenyl-methyl}-dimethyl-amine,
{[2-(4-Chloro-phenyl)-cyclohex-1-enyl]-phenyl-methyl)-dimethyl-amine and
Dimethyl-[(2-phenyl-cyclohex-1-enyl)-(4-trifluoromethyl-phenyl)-methyl]-amine.

The substituted 1-aryl-but-3-enylamine and 1-aryl-but-2-enylamine compounds of the general formula I according to the invention or the corresponding physiologically acceptable salts thereof may in each case be present in the form of the racemates thereof, the pure enantiomers thereof, the pure diastereomers thereof, or in the form of a mixture of at least two of the above-stated stereoisomers. The substituted 1-aryl-but-3-enylamine and 1-aryl-but-2-enylamine compounds of the general formula I according to the invention may likewise also in each case be present in the form of mixtures of the enantiomers or diastereomers thereof, in particular in the form of the cis/trans-diastereomers thereof. These mixtures may comprise the respective stereoisomers in any desired mixing ratio.

The present invention relates further to a process for the production of substituted 1-aryl-but-3-enylamine and 1-aryl-but-2-enylamine compounds of the above-stated general formula I, according to which at least one Mannich base of the general formula II,

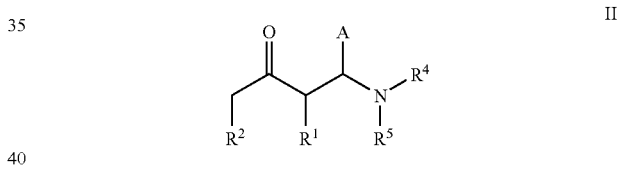

II in which $R^1$, $R^2$, $R^4$, $R^5$ and A have the above-stated meaning, is reacted with at least one organometallic compound of the general formula $R^3$-B, in which B denotes MgCl, MgBr, MgI or Li and $R^3$ has the above-stated meaning, to yield an alcohol of the general formula III,

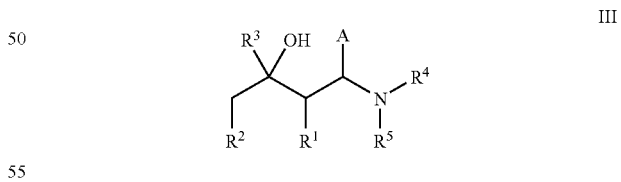

III in which the residues $R^1$ to $R^2$ and A have the above-stated meaning, and this is optionally purified by conventional methods and/or optionally isolated by conventional methods, and reacted with a suitable acid optionally in the presence of a suitable solvent to yield at least one compound of the above-stated general formula I.

The process for the production of alcohols of the general formula III is for example also described in DE 199 15 601 A1. The corresponding literature description is hereby introduced as a reference and is deemed to be part of the disclosure.

In a preferred embodiment of the process according to the invention, a protonic acid, a Lewis acid or a mixture thereof is used as suitable acid for reacting the alcohol of the general formula III to yield the compound of the general formula I.

Hydrogen bromide, hydrogen chloride, formic acid, are preferably used as the protonic acid, and trimethylsilyl iodide or chlorotrimethylsilane are preferably used as the Lewis acid.

Water may be used as suitable solvent during reaction of the alcohol of the general formula III to yield the compound of the general formula I. Moreover, organic solvents, such as for example acetonitrile, optionally also in a mixture with water, may also be used.

The temperature may vary over a wide range during reaction of the alcohol of the general formula III with the acid. The reaction is preferably performed at a temperature of 5 to 150° C., particularly preferably at a temperature of 10 to 130° C., very particularly preferably at a temperature of 15 to 120° C.

The process according to the invention may also be performed semi- or fully automatically as parallel synthesis of a group of 1-aryl-but-3-enylamine and 1-aryl-but-2-enylamine compounds of the general formula I.

The substituted 1-aryl-but-3-enylamine and 1-aryl-but-2-enylamine compounds of the general formula I according to the invention may be isolated by the process according to the invention both in the form of their free base and in the form of a salt.

Both conversion of the free base of the compounds according to the invention of the general formula I into a corresponding physiologically acceptable salt and release of the free base from the corresponding physiologically acceptable salt may proceed in accordance with conventional methods known to the person skilled in the art.

Conversion of the free base of a compound according to the invention of the general formula I into its corresponding physiologically acceptable salt may proceed for example with hydrochloric acid, hydrobromic acid, sulfuric acid, phosphoric acid, methanesulfonic acid, p-toluenesulfonic acid, carbonic acid, formic acid, acetic acid, oxalic acid, succinic acid, tartaric acid, mandelic acid, fumaric acid, lactic acid, citric acid, glutamic acid or aspartic acid. The free base of the respective compound of the general formula I according to the invention may also be converted with the free acid or a salt of a sugar substitute, such as for example saccharin, cyclamate or acesulfame, into the corresponding physiologically acceptable salt.

Conversion of the free base of a compound of the general formula I according to the invention into its corresponding hydrochloride may preferably also be obtained by combining the compound of the general formula I according to the invention, dissolved in a suitable organic solvent, such as for example butan-2-one (methyl ethyl ketone), as a free base with trimethylsilyl chloride (TMSCl).

If it is desired to separate the substituted 1-aryl-but-3-enylamine and 1-aryl-but-2-enylamine compounds of the general formula I according to the invention into their various enantiomers and/or diastereomers, this may proceed in accordance with conventional processes known to the person skilled in the art. Examples are chromatographic separation processes, in particular liquid chromatography processes at standard pressure or at elevated pressure, preferably MPLC and HPLC methods, and fractional crystallisation processes. Individual enantiomers, e.g. diastereomeric salts formed by means of HPLC on a chiral phase or by means of crystallisation with chiral acids, such as (+)-tartaric acid, (−)-tartaric acid or (+)-10-camphorsulfonic acid, may here in particular be separated from one another.

The substituted 1-aryl-but-3-enylamine and 1-aryl-but-2-enylamine compounds of the general formula I according to the invention are toxicologically safe and are therefore suitable as pharmaceutical active ingredients in pharmaceutical preparations.

The present invention therefore also provides pharmaceutical preparations which contain at least one substituted 1-aryl-but-3-enylamine or 1-aryl-but-2-enylamine compound of the general formula I according to the invention and optionally physiologically acceptable auxiliary substances.

The pharmaceutical preparations according to the invention are suitable for combatting pain or for the treatment of depression, hypotension, hypertension, senile dementia, Alzheimer's disease, general cognitive dysfunction, tinnitus, hardness of hearing, epilepsy, obesity, cachexia, urinary incontinence, for anxiolysis or for diuresis.

The use of at least one substituted 1-aryl-but-3-enylamine or 1-aryl-but-2-enylamine compound of the general formula I for the production of a pharmaceutical preparation for combatting pain, for the treatment of depression, hypotension, hypertension, senile dementia, Alzheimer's disease, general cognitive dysfunction, tinnitus, hardness of hearing, epilepsy, obesity, cachexia, urinary incontinence, for anxiolysis or for diuresis is likewise the subject matter of the present invention.

The pharmaceutical preparation according to the invention may be present as liquid, semisolid or solid dosage forms, for example in the form of solutions for injection, drops, succi, syrups, sprays, suspensions, tablets, patches, capsules, transdermal delivery systems, suppositories, ointments, creams, lotions; gels, emulsions, aerosols or in multiparticulate form, for example in the form of pellets or granules, and also administered as such.

In addition to at least one substituted 1-aryl-but-3-enylamine or 1-aryl-but-2-enylamine compound of the general formula I according to the invention, the pharmaceutical preparations according to the invention conventionally contain further physiologically acceptable pharmaceutical auxiliary substances, which are preferably selected from the group consisting of matrix materials, fillers, solvents, diluents, surface-active substances, dyes, preservatives, suspending agents, slip agents, lubricants, aromas and binders.

Selection of the auxiliary substances and the quantities thereof which are to be used depends upon whether the pharmaceutical preparation is to be administered orally, subcutaneously, parenterally, intravenously, intraperitoneally, intradermally, intramuscularly, intranasally, buccally, rectally or topically, for example onto infections of the skin, mucous membranes or eyes. Preparations in the form of tablets, coated tablets, capsules, granules, pellets, drops, succi and syrups are preferred for oral administration, while solutions, suspensions, readily reconstitutible dried preparations and sprays are preferred for parenteral, topical and inhalatory administration. Compounds according to the invention of the general formula I in a depot in dissolved form or in a dressing, optionally with the addition of skin penetration promoters, are suitable percutaneous administration preparations. Orally or percutaneously administrable preparations may also release the compounds of the general formula I according to the invention in delayed manner.

Production of the pharmaceutical preparations according to the invention may proceed with the assistance of conventional means, devices, methods and processes known to the person skilled in the art, such as are described for example in "Remington's Pharmaceutical Sciences", Ed. A. R. Gennaro, 17th ed., Mack Publishing Company, Easton, Pa. (1985), in particular in part 8, chapters 76 to 93. The corresponding literature description is hereby introduced as a reference and is deemed to be part of the disclosure.

The quantity of the respective substituted 1-aryl-but-3-enylamine or 1-aryl-but-2-enylamine compound of the general formula I according to the invention to be administered to the patient may vary and is for example dependent on the weight or age of the patient and on the mode of administration, the indication and the severity of the complaint. Conventionally, at least one substituted 1-aryl-but-3-enylamine-or 1-aryl-but-2-enylamine compound of the general formula I according to the invention is administered in a quantity of 0.005 to 500 mg/kg, in particular of 0.05 to 5 mg/kg, of patient body weight.

Pharmacological Investigations:

Analgesic Testing by Writhing Test in Mice

The investigation into analgesic efficacy was performed by phenylquinone-induced writhing in mice (modified after: I. C. Hendershot and J. Forsaith (1959) J. Pharmacol. Exp. There. 125, 237–240). Male NMRI mice weighing from 25–30 g were used for this purpose. 10 minutes after intravenous administration of the test compounds, groups of 10 animals per dose of a compound received 0.3 ml/mouse of a 0.02% aqueous solution of phenylquinone (phenylbenzoquinone, sigma, Deisenhofen; production of the solution with addition of 5% ethanol and storage in water bath at 45° C.), administered intraperitoneally. The animals were placed individually in observation cages. A push button counter was used to record the number of pain-induced stretching movements (writhing reactions=straightening of the torso with stretching of the rear extremities) for 5–20 minutes after phenylquinone administration. The control was provided by animals who received only physiological common salt solution. All the compounds were tested at the standard dosage of 10 mg/kg. The percentage inhibition (%inhibition) of the writhing reaction by a compound of the general formula I according to the invention was calculated according to the following formula:

$$\% \text{ Inhibition} = 100 - \frac{\text{Writhing reactions of treated animals}}{\text{Writhing reactions of control animals}} \times 100$$

The invention is explained below with reference to Examples. These explanations are given merely by way of example and do not restrict the general concept of the invention.

EXAMPLES

The yields of the example compounds according to the invention were not optimised.

All temperatures are uncorrected.

Production of the alcohols used in each case in the Examples given below proceeded in accordance with methods such as those described in DE 199 15 601. The corresponding literature description is hereby introduced as a reference and is deemed to be part of the disclosure.

General Procedure 1

In a synthesiser (Syro II, Multisyntech), 10 mg portions of the respective alcohol of the general formula III were combined with 2 ml of formic acid and heated for two hours to 90° C. After the reaction, the reaction mixture was evaporated in a vacuum centrifuge. The substances were analysed by means of ESI-MS. The alcohols used in each case and the compounds of the general formula I obtained by way of example are listed in Table 1 below.

TABLE 1

| Example | Alcohol of the general formula III used | 1-Aryl-but-3-enylamine or 1-aryl-but-2-enylamine compound of the general formula I |
|---|---|---|
| 1 | 2-(Dimethylamino-phenyl-methyl)-1-phenyl-cyclohexanol | Dimethyl-[phenyl-(2-phenyl-cyclohex-1-enyl)-methyl]-amine |
| 2 | 1-(4-Chloro-phenyl)-2-(dimethylamino-phenyl-methyl)-cyclohexanol | {[2-(4-Chloro-phenyl)-cyclohex-1-enyl]-phenyl-methyl}-dimethyl-amine |
| 3 | 1-Benzyl-2-(dimethylamino-phenyl-methyl)-cyclohexanol | [(2-Benzyl-cyclohex-1-enyl)-phenyl-methyl]-dimethyl-amine |
| 4 | 2-(dimethylamino-phenyl-methyl)-1-(4-fluoro-3-methylphenyl)-cyclohexanol | {[2-(4-Fluoro-3-methyl-phenyl)-cyclohex-1-enyl]-phenyl-methyl}-dimethyl-amine |
| 5 | 2-(Dimethylamino-phenyl-methyl)-1-o-tolyl-cyclohexanol | Dimethyl-[phenyl-(2-o-tolyl-cyclohex-1-enyl)-methyl]-amine |
| 6 | 1-Cyclopentyl-2-(dimethylamino-phenyl-methyl)-cyclohexanol | [(2-Cyclopentyl-cyclohex-1-enyl)-phenyl-methyl]-dimethyl-amine |
| 7 | 2-(Dimethylamino-phenyl-methyl)-1-m-tolyl-cyclohexanol | Dimethyl-[phenyl-(2-m-tolyl-cyclohex-1-enyl)-methyl]-amine |
| 8 | 2-(Dimethylamino-phenyl-methyl)-bicyclohexyl-1-ol | (Bicyclohexyl-1-en-2-yl-phenyl-methyl)-dimethyl-amine |
| 9 | 2-(Dimethylamino-phenyl-methyl)-1-(4-fluoro-phenyl)-cyclohexanol | {[2-(4-Fluoro-phenyl)-cyclohex-1-enyl]-phenyl-methyl}-dimethyl-amine |
| 10 | 2-(Dimethylamino-phenyl-methyl)-1-phenethyl-cyclohexanol | Dimethyl-[(2-phenethyl-cyclohex-1-enyl)-phenyl-methyl]-amine |
| 11 | 2-(Dimethylamino-phenyl-methyl)-1-(3-methoxyphenyl)-cyclohexanol | {[2-(3-Methoxy-phenyl)-cyclohex-1-enyl]-phenyl-methyl}-dimethyl-amine |
| 12 | 2-(Dimethylamino-phenyl-methyl-)-1-(3-phenyl-propyl)-cyclohexanol | Dimethyl-{phenyl-[2-(3-phenyl-propyl)-cyclohex-1-enyl]-methyl}-amine |
| 13 | 1-(2-Chloro-benzyl)-2-dimethylamine-phenyl-methyl)-cyclohexanol | {[2-(2-Chloro-benzyl)-cyclohex-1-enyl]-phenyl-methyl}-dimethyl-amine |
| 14 | 2-(Dimethylamino-phenyl-methyl)-1-(4-fluoro-benzyl)-cyclohexanol | {[2-(4-Fluoro-benzyl)-cyclohex-1-enyl]-phenyl-methyl}-dimethyl-amine |
| 15 | 2-(Dimethylamino-phenyl-methyl)-1-(3-methoxy-benzyl)-cyclohexanol | {[2-(3-Methoxy-benzyl)-cyclohex-1-enyl]-phenyl-methyl}-dimethyl-amine |
| 16 | 2-(Dimethylamino-phenyl-methyl)-1-(3-fluoro-benzyl)-cyclohexanol | {[2-(3-Fluoro-benzyl)-cyclohex-1-enyl]-phenyl-methyl}-dimethyl-amine |
| 17 | 2-(Dimethylamino-phenyl-methyl)-1-(2-methoxy-benzyl)-cyclohexanol | {[2-(2-Methoxy-benzyl)-cyclohex-1-enyl]-phenyl-methyl}-dimethyl-amine |
| 18 | 1-(3,5-Difluoro-benzyl)-2-(dimethylamino-phenyl-methyl)-cyclohexanol | {[2-(3,5-Difluoro-benzyl)-cyclohex-1-enyl]-phenyl-methyl}-dimethyl-amine |

General Procedure 2

The alcohol of the general formula III used in each case was refluxed with aqueous HBr, (47 wt. %; approx. 10 ml per mmol of alcohol) for five hours. The mixture was then made basic with sodium hydroxide solution (32 wt. %) and extracted three times with dichloromethane (approx. 10 ml per mmol of alcohol). The combined extracts were dried over sodium sulfate, filtered and evaporated.

The crude products obtained in this way were converted into the corresponding hydrochlorides without further purification. To this end, the respective crude product was dissolved in approx. 10 ml of 2-butanone per gram of free base, half a mol equivalent of water was then added, followed by 1.1 mol equivalents of chlorotrimethylsilane, and the mixture was stirred overnight. Then already precipitated hydrochlorides were filtered out or the hydrochlorides were precipitated by the addition of diethyl ether and/or n-hexane and then vacuum-dried.

The alcohols used in each case, the hydrochlorides obtained of the exemplary compounds of the general formula I, their yields and optionally the solvent used for precipitation of the hydrochloride are listed Table 2 below.

Example 24

Elimination with Trimethylsilyl Iodide

The alcohol 3-[2-dimethylamino-phenyl-methyl)-1-hydroxy-cyclohexyl]-phenol was dissolved or suspended in a saturated solution of sodium iodide in acetonitrile (approx. 3 ml per mmol of alcohol), three mol equivalents of trimethylchlorosilane were added dropwise and the mixture was stirred overnight.

For working up, the mixture was adjusted to pH 8 with saturated sodium hydrogencarbonate solution and then sodium thiosulfate solution was added (approx. 0.1 M) until a largely clear and colourless solution was obtained. Extraction was performed three times with diethyl ether (approx. 10 ml per mmol of alcohol), the combined extracts were dried over sodium sulfate, filtered and evaporated. The crude product thus obtained was converted into the hydrochloride without further purification. To this end, the crude product

TABLE 2

| Example | Alcohol used | 1-Aryl-but-3-enylamine or 1-aryl-but-2-enylamine compound of the general formula I | Yield of hydrochloride in g | Precipitation with |
|---|---|---|---|---|
| 19 | 2-(Dimethylamino-phenyl-methyl)-1-(2-fluoro-benzyl)-cyclohexanol | {[2-(2-Fluoro-benzyl)-cyclohex-1-enyl)-phenyl-methyl}-dimethyl-amine hydrochloride | 1.31 | |
| 20 | 1-(2-Chloro-benzyl)-2-(dimethylamine-phenyl-methyl)-cyclohexanol | {[2-(2-Chloro-benzyl)-cyclohex-1-enyl]-phenyl-methyl}-dimethyl-amine hydrochloride | 2.17 | Diethyl ether |
| 21 | 2-(Dimethylamino-phenyl-methyl)-1-(3-fluoro-benzyl)-cyclohexanol | {[2-(3-Fluoro-benzyl)-cyclohex-1-enyl)-phenyl-methyl}-dimethyl-amine hydrochloride | 0.89 | |
| 22 | 2-(Dimethylamino-phenyl-methyl)-1-(3-trifluoromethyl-benzyl)-cyclohexanol | Dimethyl-{phenyl-[2-(3-trifluoromethyl-benzyl)-cyclohex-1-enyl]-methyl}-amine hydrochloride | 2.64 | |
| 23 | 2-(Dimethylamino-phenyl-methyl)-1-phenethyl-cyclohexanol | Dimethyl-[(2-phenethyl-cyclohex-1-enyl)-phenyl-methyl]-amine hydrochloride | 1.45 | |
| 25 | 2-(Dimethylamino-phenyl-methyl)-1-(4-trifluoro-methyl-phenyl)-cyclohexanol | Dimethyl-{phenyl-(2-(4-trifluoro-methylphenyl)-cyclohex-1-enyl]-methyl}-amine | 0.75 | Diethyl ether |
| 26 | 2-Chloro-5-[2-(dimethylamino-phenyl-methyl)-1-hydroxy-cyclohexyl]-phenol | 2-Chloro-5-[6-(dimethylamino-phenyl-methyl)-cyclohex-1-enyl]-phenol | 0.63 | |
| 28 | 1-(4-Chloro-phenyl)-2-(dimethylamino-phenyl-methyl)-cyclohexanol | {[2-(4-Chloro-phenyl)-cyclohex-1-enyl]-phenyl-methyl}-dimethyl-amine hydrochloride | 1.28 | Diethyl ether |
| 29 | 2-[Dimethylamino-(4-trifluoromethyl-phenyl)-methyl]-1-phenyl-cyclohexanol | Dimethyl-[(2-phenyl-cyclohex-1-enyl)-(4-trifluoromethyl-phenyl)-methyl]-amine hydrochloride | 1.11 | n-Hexane | was dissolved in approx. 10 ml of acetone per gram of base, 1.1 mol equivalents of hydrochloric acid (32 wt. %) were added and the mixture was stirred overnight. Then the precipitated 3-[6-(dimethylamino-phenyl-methyl)-cyclohex-1-enyl]-phenol hydrochloride was filtered out and vacuum-dried.

Example 27

The alcohol 2-(dimethylamino-phenyl)-1-(4-methoxy-phenyl)-cyclohexanol was dissolved in approx. 10 ml of 2-butanone per gram of alcohol, a half mol equivalent of water was added, followed by 1.1 mol equivalents of chlorotrimethylsilane, and the mixture was stirred overnight. The precipitated {[2-(4-methoxy-phenyl)-cyclohex-2-enyl]-phenyl-methyl}-dimethylamine hydrochloride was filtered out, the corresponding base was released and purified chromatographically (silica gel, hexane/ethyl acetate 3:2). Then the purified {[2-(4-methoxy-phenyl)-cyclohex-2-enyl]-phenyl-methyl}-dimethylamine was precipitated as the hydrochloride as described above.

Pharmacological Investigations:

The in-depth investigation of the compounds of the general formula I according to the invention for analgesic efficacy was performed by phenylquinone-induced writhing in mice, as described above.

The investigated compounds according to the invention exhibited an analgesic action.

The results of selected writhing investigations are summarised in Table 3 below.

TABLE 3

Analgesic testing by writhing test on the mouse

| Example | 1-Aryl-but-3-enylamine or 1-aryl-but-2-enylamine compound of the general formula I | % Inhibition of writhing reaction* |
|---|---|---|
| 19 | {[2-(2-Fluoro-benzyl)-cyclohex-1-enyl]-phenyl-methyl}-dimethyl-amine | 87% (10 mg/kg) |
| 20 | {[2-(2-Chloro-benzyl)-cyclohex-1-enyl]-phenyl-methyl}-dimethyl-amine | 63% (10 mg/kg) |
| 21 | {[2-(3-Fluoro-benzyl)-cyclohex-1-enyl]-phenyl-methyl}-dimethyl-amine | 67% (10 mg/kg) |
| 22 | Dimethyl-{phenyl-[2-(3-trifluoromethyl-benzyl)-cyclohex-1-enyl]-methyl}-amine | 46% (21.5 mg/kg) |
| 23 | Dimethyl-[(2-phenethyl-cyclohex-1-enyl)-phenyl-methyl]-amine | 67% (10 mg/kg) |
| 24 | 3-[6-(Dimethylamino-phenyl-methyl)-cyclohex-1-enyl]-phenol hydrochloride | 76% (10 mg/kg) |
| 27 | {[2-(4-Methoxy-phenyl)-cyclohex-2-enyl]-phenyl-methyl}-dimethyl-amine hydrochloride | 47% (10 mg/kg) |
| 28 | {[2-(4-Chloro-phenyl)-cyclohex-1-enyl]-phenyl-methyl}-dimethyl-amine hydrochloride | 71% (10 mg/kg) |
| 29 | Dimethyl-[(2-phenyl-cyclohex-1-enyl)-(4-trifluoromethyl-phenyl)-methyl]-amine hydrochloride | 40% (10 mg/kg) |

*The dosage for intravenous administration is stated in brackets.

The invention claimed is:

1. Substituted 1-aryl-but-3-enylamine and 1-aryl-but-2-enylamine compounds of the formula I,

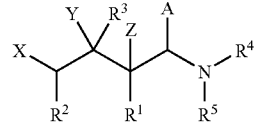

in which
R$^1$ and R$^2$, identical or different, denote a C$_{1-6}$ alkyl group or together form a ring as (CH$_2$)$_{2-6}$, which may also be substituted or benzo-fused with at least one optionally at least mono-substituted aryl or heteroaryl group,
R$^3$ denotes a C$_{3-6}$ alkyl, a C$_{3-7}$ cycloalkyl, an optionally at least mono-substituted aryl or heteroaryl group or an optionally at least mono-substituted aryl or heteroaryl group attached via a C$_{1-3}$ alkylene group,
R$^4$ and R$^5$, identical or different, denote a C$_{1-6}$ alkyl, a C$_{3-7}$ cycloalkyl, a phenyl, a benzyl or a phenethyl group or R$^4$ and R$^5$ together form a ring as (CH$_2$)$_{3-6}$ or —CH$_2$—CH$_2$—O—CH$_2$—CH$_2$,
X and Y or Y and Z together denote a bond,
A denotes an optionally at least mono-substituted aryl or heteroaryl group,
in the form of the racemates, diastereomers or enantiomers thereof as a free base or a corresponding physiologically acceptable salt.

2. Substituted 1-aryl-but-3-enylamine and 1-aryl-but-2-enylamine compounds according to claim 1, characterised in that R$^1$ and R$^2$ together form a (CH$_2$)$_{2-6}$ ring, which may also be substituted or benzo-fused with at least one optidnally at least mono-substituted aryl or heteroaryl group.

3. Substituted 1-aryl-but-3-enylamine and 1-aryl-but-2-enylamine compounds according to claim 1, characterised in that R$^1$ and R$^2$ together form a cyclohexyl ring, which may also be substituted with an optionally at least mono-substituted phenyl group.

4. Substituted 1-aryl-but-3-enylamine and 1-aryl-but-2-enylamine compounds according to claim 1, characterised in that R$^3$ denotes an optionally at least mono-substituted aryl group or an optionally at least mono-substituted aryl group attached via a C$_{1-3}$ alkylene group.

5. Substituted 1-aryl-but-3-enylamine and 1-aryl-but-2-enylamine compounds according to claim 1, characterised in that the groups R$^4$ and R$^5$, identical or different, denote a C$_{1-6}$ alkyl group or together form a —(CH$_2$)$_5$— or —CH$_2$—CH$_2$—O—CH$_2$—CH$_2$ ring.

6. Substituted 1-aryl-but-3-enylamine and 1-aryl-but-2-enylamine compounds according to claim 1, characterised in that X and Y together denote a bond.

7. Substituted 1-aryl-but-3-enylamine and 1-aryl-but-2-enylamine compounds according to claim 1, characterised in that A denotes an optionally at least mono-substituted aryl group.

8. Substituted 1-aryl-but-3-enylamine and 1-aryl-but-2-enylamine compounds according to claim 1:
Dimethyl-[phenyl-(2-phenyl-cyclohex-1-enyl)-methyl]-amine,
{[2-(4-Chloro-phenyl)-cyclohex-1-enyl]-phenyl-methyl}-dimethyl-amine,
[(2-Benzyl-cyclohex-1-enyl)-phenyl-methyl]-dimethylamine, {[2-(4-Fluoro-3-methyl-phenyl)-cyclohex-1-enyl]-phenyl-methyl}-dimethyl-amine,
Dimethyl-[phenyl-(2-o-tolyl-cyclohex-1-enyl)-methyl]-amine,
[(2-Cyclopentyl-cyclohex-1-enyl)-phenyl-methyl]-dimethyl-amine,
Dimethyl-[phenyl-(2-m-tolyl-cyclohex-1-enyl)-methyl]-amine,
(Bicyclohexyl-1-en-2-yl-phenyl-methyl)-dimethyl-amine,
{[2-(4-Fluoro-phenyl)-cyclohex-1-enyl]-phenyl-methyl}-dimethyl-amine,
Dimethyl-[(2-phenethyl-cyclohex-1-enyl)-phenyl-methyl]-amine,
{[2-(3-Methoxy-phenyl)-cyclohex-1-enyl]-phenyl methyl}-dimethyl-amine,
Dimethyl-{phenyl-[2-(3-phenyl-propyl)-cyclohex-1-enyl]-methyl}-amine,
{[2-(2-Chloro-benzyl)-cyclohex-1-enyl]-phenyl-methyl}-dimethyl-amine, }[2-(4-Fluoro-benzyl)-cyclohex-1-enyl]-phenyl-methyl}-dimethyl-amine,
{[2-(3-Methoxy-benzyl)-cyclohex-1-enyl]-phenyl methyl}-dimethyl-amine,
{[2-(3-Fluoro-benzyl)-cyclohex-1-enyl]-phenyl-methyl}-dimethyl-amine,
{[2-(2-Methoxy-benzyl)-cyclohex-1-enyl]-phenyl-methyl}-dimethyl-amine,
{[2-(3, 5-Difluoro-benzyl)-cyclohex-1-enyl]-phenyl-methyl}-dimethyl-amine,
{[2-(2-Fluoro-benzyl)-cyclohex-1-enyl]-phenyl-methyl}-dimethyl-amine,
{[2-(2-Chloro-benzyl)-cyclohex-1-enyl]-phenyl-methyl}-dimethyl-amine,
{[2-(3-Fluoro-benzyl)-cyclohex-1-enyl]-phenyl-methyl)-dimethyl-amine,
Dimethyl-{phenyl-[2-(3-trifluoromethyl-benzyl)-cyclohex-1-enyl]-methyl}-amine,
Dimethyl-[(2-phenethyl-cyclohex-1-enyl)-phenyl-methyl}-amine,
3-[6-(Dimethylamino-phenyl-methyl)-cyclohex-1-enyl]-phenol,
Dimethyl-{phenyl-(2-(4-trifluoromethylphenyl)-cyclohex-1-enyl]-methyl}-amine,
2-Chloro-5-[6-(dimethylamino-phenyl-methyl)-cyclohex-1-enyl]-phenol,
{[2-(4-Methoxy-phenyl)-cyclohex-2-enyl]-phenyl-methyl}-dimethyl-amine,
{[2-(4-Chioro-phenyl)-cyclohex-1-enyl]-phenyl-methyl}-dimethyl-amine,
Dimethyl-[(2-phenyl-cyclohex-1-enyl)-(4-trifluoromethyl-phenyl)-methyl]-amine,
and the corresponding physiologically acceptable salts.

9. A process for the production of substituted 1-aryl-but-3-enylamine and 1-aryl-but-2-enylamine compounds of the formula I according to claim 1, characterised in that at least one Mannich base of the formula II,

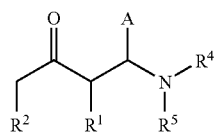

II in which $R^1$, $R^2$, $R^4$, $R^5$ and A have the meaning according to the formula I according to claim 1, is reacted with at least one organometallic compound of the formula $R^3$—B, in which B denotes MgCl, MgBr, MgI or Li and $R^3$ has the meaning according to the formula I according to claim 1, to yield at least one alcohol of the formula III,

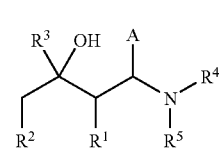

III in which the groups $R^1$ to $R^5$ and A have the meaning according to the formula I according to claim 1, and this is optionally purified by conventional methods and/or optionally isolated by conventional methods, and reacted with a suitable acid optionally in the presence of a suitable solvent to yield at least one compound of the formula I according to claim 1.

10. A process according to claim 9, characterised in that a protonic acid, a Lewis acid or a mixture thereof is used as suitable acid.

11. A process according to claim 10, characterised in that hydrogen bromide, hydrogen chloride or formic acid is used as protonic acid.

12. A process according to claim 10, characterised in that trimethylsilyl iodide or chlorotrimethylsilane is used as the Lewis acid.

13. A process according to claim 9, characterised in that reaction of the alcohol with the acid is performed at a temperature of 5 to 150° C.

14. A pharmaceutical preparation containing at least one substituted 1-aryl-but-3-enylamine or 1-aryl-but-2-enylamine compound according to claim 1 and optionally physiologically acceptable auxiliary substances.

15. A pharmaceutical preparation according to claim 14 for combatting pain.

16. A pharmaceutical preparation according to claim 14 for the treatment of depression.

17. A pharmaceutical preparation according to claim 14 for the treatment of hypotension.

18. A pharmaceutical preparation according to claim 14 for the treatment of hypertension.

19. A pharmaceutical preparation according to claim 14 for the treatment of senile dementia.

20. A pharmaceutical preparation according to claim 14 for the treatment of tinnitus.

21. A pharmaceutical preparation according to claim 14 for the treatment of hardness of hearing.

22. A pharmaceutical preparation according to claim 14 for the treatment of epilepsy.

23. A pharmaceutical preparation according to claim 14 for the treatment of obesity.

24. A pharmaceutical preparation according to claim 14 for the treatment of cachexia.

25. A pharmaceutical preparation according to claim 14 for the treatment of urinary incontinence.

26. A pharmaceutical preparation according to claim 14 for anxiolysis.

27. A pharmaceutical preparation according to claim 14 for diuresis.

28. A method of treating pain, depression, hypotension, hypertension, senile dementia, Alzheimer's disease, general cognitive dysfunction, tinnitus, hardness of hearing, epilepsy, obesity, cachexia or urinary incontinence or for anxiolysis or diuresis comprising administering to a patient in need thereof a therapeutic amount of a pharmaceutical preparation comprising at least one substituted 1-aryl-but-3-enylamine or 1-aryl-but-2-enylamine compound according to claim 1.

29. A substituted 1-aryl-but-3-enylamine and 1-aryl-but-2-enylamine compounds according to claim 4, characterised in that $R^3$ denotes an optionally at least mono-substituted phenyl, benzyl or phenethyl group attached via a $C_{1-3}$ alkylene group.

30. Substituted 1-aryl-but-3-enylamine and 1-aryl-but-2-enylamine compounds according to claim 7, characterised in that A denotes an optionally at least mono-substituted phenyl group.

31. A compound of claim 8 where the corresponding physiologically acceptable salt is the hydrochloride thereof.

32. A process according to claim 9, characterised in that reaction of the alcohol with the acid is performed at a temperature of 15 to 120° C.

33. A process according to claim 9, characterised in that reaction of the alcohol with the acid is performed at a temperature of 10 to 130° C.

34. Substituted 1-aryl-but-3-enylamine and 1-aryl-but-2-enylamine compounds according to claim 1, characterised in that the groups $R^4$ and $R^5$, identical or different, denote a $C_{1-2}$ alkyl group.

* * * * *